United States Patent
Rosenland et al.

(10) Patent No.: US 10,132,772 B2
(45) Date of Patent: Nov. 20, 2018

(54) SENSOR ELEMENT HAVING A CONTACT SURFACE

(71) Applicant: Robert Bosch GmbH, Stuttgart (DE)

(72) Inventors: Marc Rosenland, Hohenhaslach (DE); Andreas Rottmann, Stettfeld (DE); Carsten Gallinger, Leonberg (DE); Markus Lux, Winnenden (DE); Frank Buse, Stuttgart (DE); Jens Schneider, Leonberg (DE); Thomas Juestel, Hirschaid-Juliushof (DE)

(73) Assignee: ROBERT BOSCH GMBH, Stuttgart (DE)

( * ) Notice: Subject to any disclaimer, the term of this patent is extended or adjusted under 35 U.S.C. 154(b) by 195 days.

(21) Appl. No.: 14/900,236

(22) PCT Filed: Mar. 13, 2014

(86) PCT No.: PCT/EP2014/055004
§ 371 (c)(1),
(2) Date: Dec. 21, 2015

(87) PCT Pub. No.: WO2014/202244
PCT Pub. Date: Dec. 24, 2014

(65) Prior Publication Data
US 2016/0153928 A1    Jun. 2, 2016

(30) Foreign Application Priority Data
Jun. 21, 2013 (DE) ........................ 10 2013 211 791

(51) Int. Cl.
    *G01N 27/40*     (2006.01)
    *G01N 27/407*     (2006.01)
(Continued)

(52) U.S. Cl.
CPC ...... *G01N 27/4071* (2013.01); *G01M 15/104* (2013.01); *G01N 27/4067* (2013.01)

(58) Field of Classification Search
CPC .......... G01N 27/4071; G01N 27/4067; G01M 15/104
See application file for complete search history.

(56) References Cited

U.S. PATENT DOCUMENTS

2011/0139618 A1    6/2011   Serrels et al.

FOREIGN PATENT DOCUMENTS

DE    19937163 A1    2/2001
DE    102 08 533    9/2003
(Continued)

OTHER PUBLICATIONS

English Machine Translation of Wahl et al., DE 10 2004 050226 A1, Apr. 20, 2006, Translated Aug. 2017.*
(Continued)

*Primary Examiner* — David Z Huang
(74) *Attorney, Agent, or Firm* — Norton Rose Fulbright US LLP; Gerard Messina

(57) ABSTRACT

A sensor element, in particular for detection of a physical property of a gas, in particular for detection of the concentration of a gas component or of the temperature or of a solid constituent or of a liquid constituent of an exhaust gas of an internal combustion engine, the sensor element including, a solid electrolyte film and including, located oppositely from one another in its longitudinal direction, first and second end regions, the sensor element including outside the second end region, in particular in the first end region, a functional element electrically conductively connected to a contact surface disposed in the second end region on the outer surface of the sensor element, the contact surface having a rounding, which is a radius, on its side facing away from the (Continued)

first end region. The contact surfaces each include three sub-regions: head region, neck region, and body region.

17 Claims, 6 Drawing Sheets

(51) Int. Cl.
  *G01M 15/10* (2006.01)
  *G01N 27/406* (2006.01)

(56) References Cited

FOREIGN PATENT DOCUMENTS

| | | |
|---|---|---|
| DE | 10 2004 047 783 | 4/2006 |
| DE | 10 2004 050 226 | 4/2006 |
| DE | 10 2006 055 797 | 5/2008 |
| DE | 10 2009 055 416 | 7/2011 |
| EP | 2 141 492 | 1/2010 |
| JP | H0371021 A | 3/1991 |
| JP | H0461056 U | 5/1992 |
| JP | 2013083629 A | 5/2013 |
| WO | 2009006290 A1 | 1/2009 |
| WO | 2009074471 A1 | 6/2009 |

OTHER PUBLICATIONS

English Machine Translation of Renger et al., DE 10 2006 055797 A1, May 29, 2008, Translated Aug. 2017.*

* cited by examiner

SENSOR ELEMENT HAVING A CONTACT SURFACE

FIELD OF THE INVENTION

The present invention proceeds from known sensor elements that are used, for example, as exhaust gas sensors, in particular as lambda probes, which have become very widespread in motor vehicles. The invention is nevertheless also applicable to other types of sensor elements, for example to sensors for detecting other gaseous constituents of exhaust gases, and to particle sensors or the like. The invention relates in particular to a sintered or sinterable ceramic sensor element that is manufactured, for example, by bringing together, in particular stacking on top of one another, individual, optionally imprinted, green ceramic films.

BACKGROUND INFORMATION

The sensor element encompasses in particular at least one electrical, electrochemical, and/or electronic functional element in a first end region, as a rule facing toward the exhaust gas, of the sensor element. A capability for supplying electricity to the sensor element is provided in the present case by a contact surface on the outer surface of the sensor element in a second region, as a rule facing away from the exhaust gas.

In addition to electrical conductivity, the contact surface is required to have high temperature resistance and chemical resistance during operation and during manufacture of the sensor element. Noble metals, for example platinum and the like, are therefore commonly used. Because such noble metals are comparatively expensive, it is generally desirable to reduce the size of the contact surface as much as possible.

On the other hand, making the contact surface smaller is to be regarded as critical if contacting can no longer be reliably ensured under all circumstances as a result of production tolerances of the sensor element or as a result of production tolerances of contact elements interacting with the sensor element in a sensor, for example metal wires, pins, springs, or the like.

Sensor elements having contact surfaces are already believed to be understood from DE 102 08 533 A1, DE 10 2004 047 783 A1, and DE 10 2009 055 416 A1. These contact surfaces are embodied rectangularly in their end regions facing away from the functional elements.

SUMMARY OF THE INVENTION

Sensor elements according to the present invention having the features described herein have the advantage that they or their contact surfaces can be manufactured with decreased material usage and thus economically, without possibly resulting in more assembly errors in conjunction with electrical contacting.

For this, provision is made according to the present invention that the contact surface has a rounding on its side facing away from the first end region.

Investigations regarding production fluctuations in the relative position of a contact surface and associated contact element after, in particular, rapidly cycled automated assembly have shown that relative positional fluctuations occur in both a longitudinal direction and a transverse direction, so that a decrease in the length and width of the contact surfaces would result, given the corresponding variations, in assembly errors.

The same investigations have also shown that the fluctuations in a longitudinal direction in the relative position of a contact surface and associated contact element after, in particular, automated assembly are not correlated, or are only negligibly weakly correlated, with the fluctuations in a transverse direction.

The result is therefore that rectangular contact surfaces used for test purposes, which are of just sufficiently large dimensions, are hit by the contact element with a certain frequency both in their edge regions in a longitudinal direction and in their edge regions in a transverse direction. These rectangular contact surfaces are, however, hit by the contact elements with a practically vanishingly low frequency in the corner regions facing away from the exhaust gas. In light of this it becomes clear why the rounding of the contact surfaces in these regions does not increase the frequency of assembly errors.

The rounding provided according to the present invention thus also makes it possible, in particular, to make the contact surface smaller, in particular including in sensor elements that are themselves not miniaturized or are miniaturized only to a certain degree, and which are subject to more stringent assembly requirements. The result is that the planar area of a contact surface, of several contact surfaces, or of all contact surfaces of the sensor element (in a plan view of the sensor element or in a plan view of the largest surface of the sensor element) can be reduced respectively to 2% or less of the planar area of the largest surface of the sensor element, in particular even to respectively 1.5% or less of the planar area of the largest surface of the sensor element.

Additionally or alternatively, the length of a contact surface, of several contact surfaces, or of all contact surfaces of the sensor element can be reduced to 9% or less of the length of the sensor element, in particular even to 8% or less of the length of the sensor element. Additionally or alternatively, the width of a contact surface, of several contact surfaces, or of all contact surfaces of the sensor element can be reduced to 35% or less of the width of the sensor element, in particular even to 31.5% or less of the width of the sensor element.

The invention can also advantageously relate, in particular, to sensor elements whose height (sintered) is not less than 1.2 mm and/or whose length (sintered) is not less than 50 mm and/or whose width (sintered) is not less than 4.5 mm, and which are thus subject to more stringent assembly requirements. The dimensions for unsintered sensor elements are 25% greater.

The terms "longitudinal direction," "transverse direction," and "vertical direction" are used in the context of this Application, in principle, merely for purposes of a rectilinear reference system. In particular, however, these can moreover be directions that are identified by the sensor element; for example, in an (in particular) cuboidal sensor element, the longitudinal direction can be the direction in which the longest lateral edges of the sensor element point, the vertical direction can be the direction in which the shortest lateral edges of the sensor element point, and/or the transverse direction can be the direction in which those lateral edges of the sensor element which have an intermediate length point. In the case of a rod-shaped sensor element, for example, the longitudinal direction can point in the direction of an axis around which the rod-shaped sensor element is rotationally symmetrical or substantially rotationally symmetrical.

When reference is made only "substantially" to a direction, relevant directions, besides the direction in the strict sense, are also ones that deviate slightly from that direction, for example by no more than 15°, and/or directions that are at least not orthogonal to that direction. In addition, a direction is also substantially realized by a structure when the relevant structure deviates only in a small sub-region that, for example, encompasses no more than 10% of the structure.

A "length of the sensor element" is understood in the context of this Application as the extent of the sensor element in a longitudinal direction, a "width of the sensor element" as the extent of the sensor element in a transverse direction, and a "height of the sensor element" as the extent of the sensor in a vertical direction. This direction is also relevant for the plan view of the sensor element.

The term "end region of the sensor element" is understood in principle in the context of this Application, with reference to a longitudinal direction, merely as a continuous sub-region of the sensor element that encompasses the pertinent end of the sensor and constitutes no more than 50% of the length of the sensor element. In this regard, an end region and an oppositely located end region intersect, for example, only in a surface. In somewhat more restricted fashion, an end region of the sensor element can also be understood in particular as a continuous sub-region of the sensor element that encompasses the relevant end of the sensor and constitutes no more that a third or even no more than a quarter of the length of the sensor element.

The term "functional element" is, in principle, not to be construed narrowly in the present case. For example, it can refer to a noble-metal electrode or cermet electrode communicating with the external space of the sensor element, and/or to an electrical resistance heater that exhibits, in particular, an electrical resistance of at most 30 ohms at 20° C., and/or to the like.

The term "contact surface rounded on one side" is understood in principle, in the context of this Application, to mean merely that the contact surface can be imagined to proceed from a rectangular contact surface of the same length and the same width, from which material has been removed on the pertinent side in at least one corner region.

Although the contour resulting therefrom can be entirely or locally of circular-arc shape, in particular in the narrow mathematical sense, and in particular can encompass an arc of 90° or 180°, what applies in principle is merely the removal of material from the corner regions. A beveling or chamfering is also, in this sense, encompassed by the term "rounding."

Whereas in the first instance the term "radius of curvature" results in natural fashion, in the case of roundings that are not of circular-arc shape in the strictly mathematical sense it is defined by the radius of curvature of the circular-arc-shaped rounding which differs the least, on average, from the actual contour. This will be explained below in further detail with reference to examples.

Advantageous expressions of the invention provide that the radius of curvature is equal to or exceeds a certain minimum size. The advantageous effects of the invention are then particularly expressed. In addition to metric minimum sizes, for example 0.3 mm, 0.4 mm, 0.5 mm, or 0.6 mm for sintered sensor elements, minimum dimensions that are measured as a proportion of the width of the sensor element, for example 6%, 8%, 10%, or 12%, and/or are measured as a proportion of the width of the contact surface, for example 15%, 23%, 30%, or 45%, are alternatively or additionally appropriate.

In the advantageous extreme case the rounding is maximal, i.e. the end portion of the contact surface is semicircular or similar to a semicircle. The radius of curvature is then defined by half the width of the contact surface.

Special embodiments of the invention relate to sensor elements in which in addition to the contact surface, a further contact surface is disposed in the end region located opposite the functional element, for example alongside one another.

The further contact surface either can contact the same functional element as the contact surface, for example an electrical heater, or can contact a different functional element from the contact surface, for example a further electrode.

In principle, the further contact surface can likewise be configured in accordance with a feature indicated for the contact surface in the context of this Application, or a feature combination indicated for the contact surface in the context of this Application. In particular, the contact surface and the further contact surface can be mirror-symmetrical or substantially mirror-symmetrical with respect to an axis that extends in a longitudinal direction of the sensor element, in particular centeredly in the transverse direction with respect to the sensor element.

In the case of two contact surfaces, a spacing is embodied between the contact surfaces which as a rule is dimensioned to be sufficiently large that a shunt between the contact surfaces is reliably ruled out even in the context of production fluctuations and production imperfections ("smearing"). An insulation resistance between the contact surfaces on the order of a megaohm at room temperature (20° C.) and on the order of a hundred thousand ohm at maximum operating temperature (e.g. 400° C.), is typically required.

Investigations by the Applicant have shown that the shunt resistance between the contact surfaces increases further as a result of the rounding of one or even both contact surfaces in the manner according to the present invention, in particular mutually facing corner regions of the contact surfaces. This is the case even when the spacing between the contact surfaces (shortest connection) is not decreased by the notional operation of rounding. This effect is presumably attributable to potential spikes or field strength maxima, etc. occurring in the region of sharp corners.

In this context it may be in turn that the radius of curvature be equal to, or exceed, a certain minimum value. The advantageous effects of the invention are then particularly pronounced. The radius of curvature may be equal to more than the spacing between the contact surfaces embodied on the sensor element, or more than a proportion of the spacing of the contact surfaces embodied on the sensor element, for example 10%, 30%, or 50%.

Special embodiments of the invention relate to sensor elements having at least one contact surface that interacts with a functional element disposed in the interior of the sensor element and/or with a conductor path disposed in the interior of the sensor element. Electrical connection of the contact surface to regions located in the interior of the sensor is accomplished via a passthrough that, proceeding from the contact surface, for example perpendicularly to the contact surface, leads into the interior of the sensor element, and is known per se from the existing art, for example from DE 102009028194 A1.

It is significant that the passthrough represents a region of the electrical connection between contact surface and functional element which is mechanically and electrically sensitive in terms of production engineering. For this reason it is desirable that the region in which the passthrough encounters the contact surface not interact mechanically with a contact element that electrically contacts the sensor element at the contact surface, for example nonpositively, from outside the sensor element.

Provision is therefore made in particular that the contact surface encompass a first region (hereinafter a "body region") that is provided for mechanical interaction with a contact element, and a second region (hereinafter a "head region") that is not provided for mechanical interaction with a contact element but instead represents the connection to the passthrough.

While the body region is embodied in particular in oval fashion with straight lateral edges, the head region is embodied, in particular, in circular or annular fashion. Embodied between the body region and head region is a third region (hereinafter a "neck region") whose function is to space the body region and head region apart in electrically connected fashion with minimized material usage. In order to minimize material usage while ensuring contactability and electrical connection between the contact surface and functional element, provision is made that in the neck region the width of the contact surface is less than in the body region and in the head region, specifically at least 5% or even 25% with respect to the head region, and/or respectively at least 15% or even 50% with respect to the body region.

In order not to displace the passthroughs too far toward the functional element, where elevated temperatures and thus reduced insulation strengths are generally present, it is advantageous to limit the longitudinal extent of the neck region, for example, to a length that is less than the longitudinal extent of the body region and/or of the head region.

It has furthermore been found to be advantageous to orient the passthroughs, proceeding from contact surfaces disposed off-center in the transverse direction of the sensor elements, toward the sensor center in a transverse direction. The head regions of the contact surfaces are also, correspondingly, to be oriented toward the sensor center in a transverse direction.

In a particular refinement of the invention this is achieved in that the body region of the contact region additionally has a first axis of symmetry that extends in particular in a longitudinal direction of the sensor element, and the head region and neck region of the contact surface have a common second axis of symmetry, and the first axis of symmetry and second axis of symmetry enclose an angle, in particular, of 5° to 25°.

A specific choice of materials for conductor paths, supply leads, passthroughs, and contact surfaces can furthermore be useful in connection with the present invention. Materials having a noble-metal proportional content of 83 wt % or more may be used here in principle, so that defined ohmic resistance values can be achieved with minimized noble-metal usage. Noble-metal proportional contents of 95 wt % or more, for example 98 wt %, may in fact be used for at least one supply lead to the heating apparatus. A proportional content of at least 1 wt % Al2O3, better in fact at least 1.5 wt % Al2O3, which may be at most 2.5 wt % Al2O3, has proven to be favorable for precise adjustability of the electrical resistance of these structures. At least one supply lead to the heating apparatus can be configured integrally with the heating apparatus and from the same material.

Additionally or alternatively, a lower noble-metal proportional content than for the at least one supply lead to the heating apparatus is provided for the supply lead to the cermet electrode and/or for at least one contact surface, which may be for example 83 wt % to 87 wt %, a proportional content of ZrO2 and Y2O3 together of 12 wt % to 16 wt % being provided in particular in the supply lead to the cermet electrode. The advantage is that the supply lead to the cermet electrode can be manufactured together with the cermet electrode in one process step and from the same material. An Al2O3 content, which may be 0.2 wt % to 1 wt %, is also advantageous respectively for the supply lead to the cermet electrode and for the cermet electrode.

Additionally or alternatively, a lower noble-metal proportional content than for the at least one supply lead to the heating apparatus is provided for at least one passthrough, which may be for example 83 wt % to 87 wt %, a proportional content of ZrO2 and Y2O3 together of 3 wt % to 8 wt %, and additionally an Nb2O5 proportional content of 6 wt % to 12 wt %, being provided in the passthrough. The advantage is that the passthroughs can be handled better in the production process. In particular, corresponding pastes have better rheological properties and enable better ceramic attachment of the passthroughs inside the sensor elements. In conjunction with sensor elements that are made predominantly of YSZ, a further result is that oxygen ion conductivity in the edge regions of the passthroughs is decreased, which improves the functionality of the sensor elements.

The noble-metal proportional contents recited above can be constituted in particular from platinum. Alternatively, in particular with regard to at least one passthrough, in order to stabilize the metal phase there can be proportional contents of rhodium, which may be 0.2 wt % to 0.8 wt % based on the total composition of the materials, and/or proportional contents of palladium, which may be 0.2 wt % to 1 wt % based on the total composition of the materials.

Further noble-metal proportional contents can always be provided.

DETAILED DESCRIPTION

Figure 1:
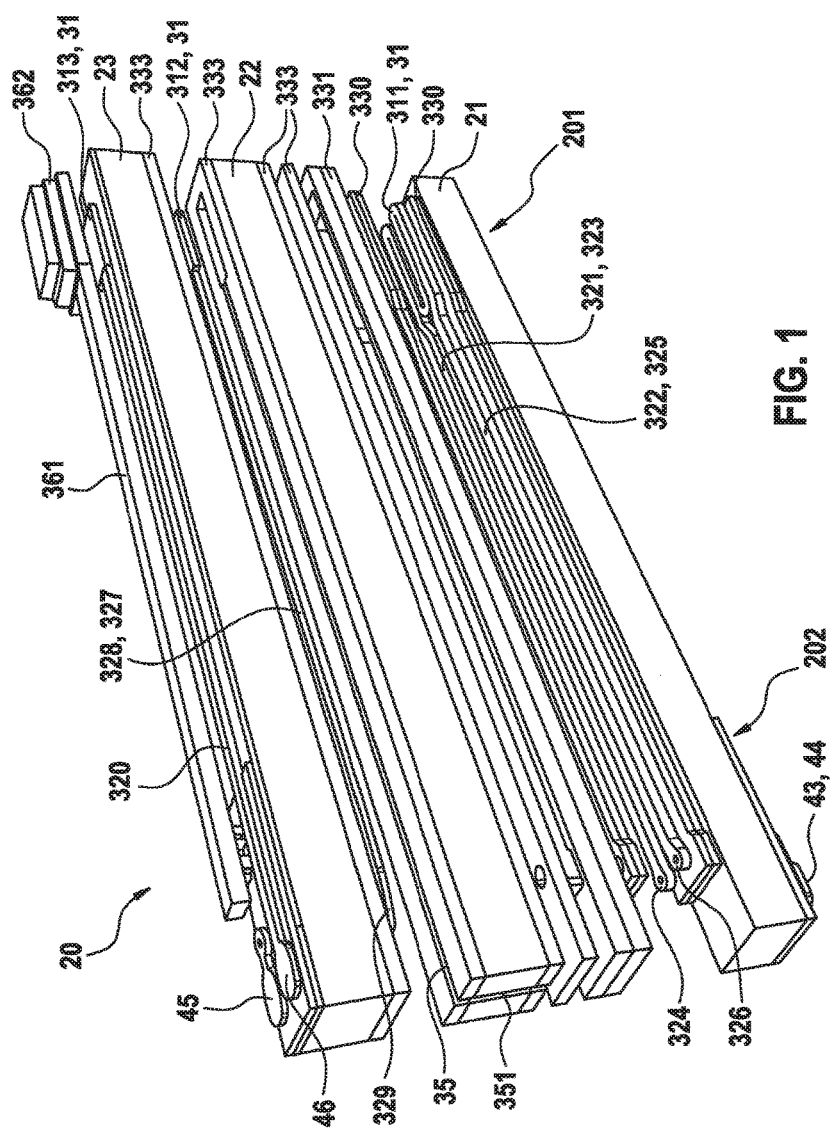
FIG. 1 is a schematic perspective exploded view of a sensor element according to the present invention.

FIG. 1 shows, as an exemplifying embodiment of the invention, an overall view of a sensor element 20 that can be disposed in a housing of a gas sensor (not depicted) that serves to determine the oxygen concentration in an exhaust gas of an internal combustion engine (not depicted). Equipped with corresponding functional elements, the invention is of course also suitable for sensor elements for other sensors, for example sensors for particle measurement.

The sensor element extends in FIG. 1 in the longitudinal direction from left to right, a first end region 201 of sensor element 20 being depicted on the right and a second end region 202 of sensor element 20 on the left. When installed and operated as intended, first end region 201 of sensor element 20 faces toward an exhaust gas, and second end region 202 of sensor element 20 faces away from the exhaust gas.

In addition, sensor element 20 extends in FIG. 1 in a transverse direction from front to back, and in a vertical direction from bottom to top.

Sensor element 20 is constructed from imprinted ceramic layers that are embodied in this example as a first, a second, and a third solid electrolyte film 21, 22, 23, and contain yttria-stabilized zirconium oxide (YSZ). In the example, solid electrolyte films 21, 22, 23 have a length of 72 mm, a width of 5 mm, and a height of 540 µm before a sintering operation. Films of a sintered sensor element 20 have 20% shorter edge lengths.

Figure 3:
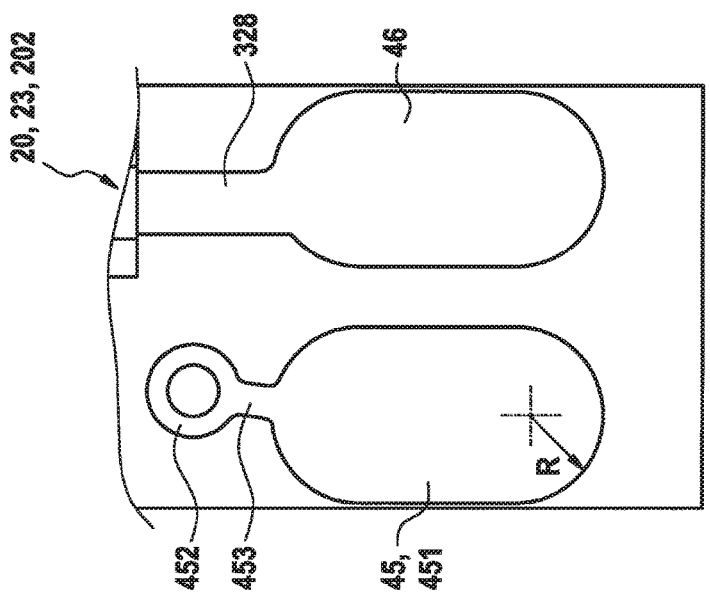

First solid electrolyte film 21 is equipped, here imprinted, on its large surface facing outward from the viewpoint of sensor element 20 (downward in FIG. 1), in second end region 202 of sensor element 20, with a contact surface 43 and a further contact surface 44 (see also FIG. 3).

First solid electrolyte film 21 is equipped on its large surface facing inward from the viewpoint of sensor element 20 (upward in FIG. 1), in first end region 201 of sensor element 20, with a meander-shaped heating apparatus 311 as a functional element 31 that serves to heat first end region 201 of sensor element 20. Attached as a continuation of the meander-shaped heating apparatus 311 at each of its ends is a respective conductor path 321, 322, the transition from heating apparatus 311 to conductor path 321, 322 being characterized by an increase in the structure width and/or structure height, or a decrease in electrical resistance per unit length.

Conductor paths 321, 322 have on the exhaust-gas side a portion, referred to as supply lead 323, 325, that in the present case has a constant width. Conductor paths 321, 322 further have, facing away from the exhaust gas, a portion referred to as a collar 324, 326 that in the present case is embodied annularly (see also FIG. 4).

First solid electrolyte film 21 is furthermore equipped, here imprinted, on its large surface facing inward from the viewpoint of sensor element 20 (upward in FIG. 1), with insulating layers 330 and with a sealing frame 331, and with a film binder layer 333.

Figure 6:
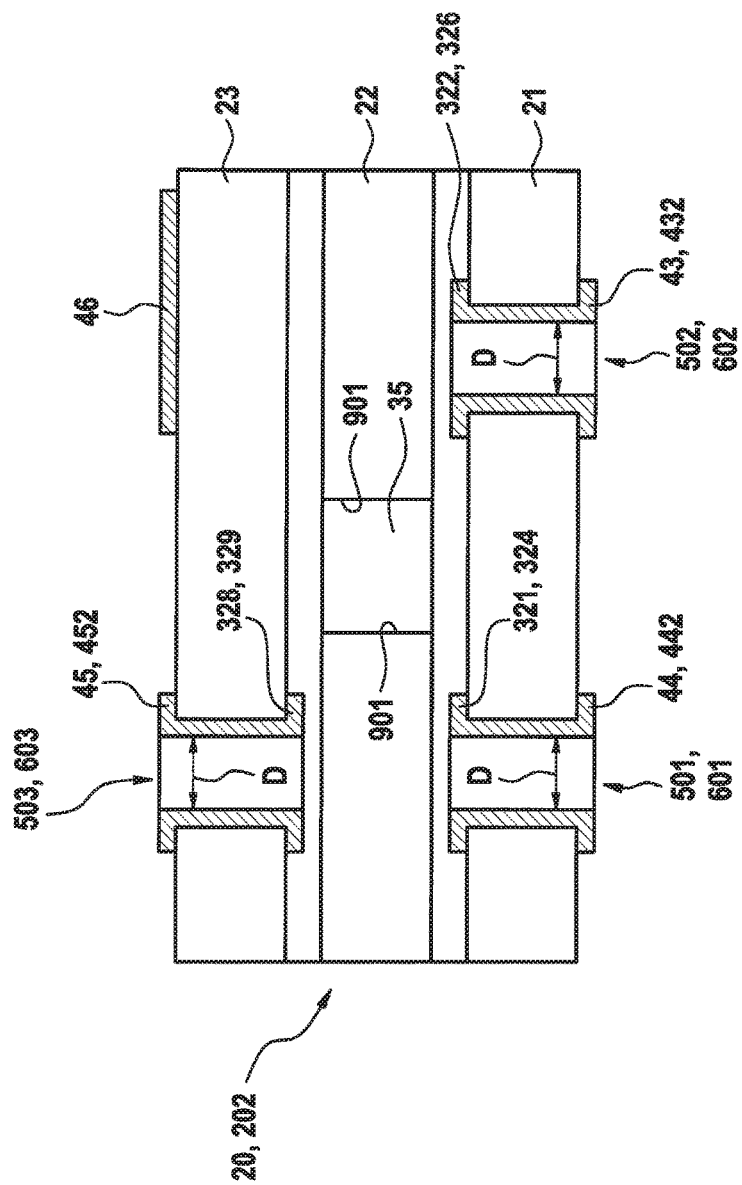

First solid electrolyte film 21 has in second end region 202 two passthroughs 501, 502 that extend in a vertical direction through first solid electrolyte film 21 and respectively electrically conductively connect a contact surface 43, 44 to a collar 324, 326 of a conductor path 321, 322 (see FIG. 6).

Second solid electrolyte film 22 is equipped on both sides with a respective film binder layer 333; second solid electrolyte film 22 furthermore has a reference gas conduit 35 that extends lengthwise from a reference gas opening 351, disposed facing away from the exhaust gas, into first end region 201 of sensor element 20, and proceeds centeredly in a transverse direction. Reference gas conduit 35 is embodied in unfilled fashion; in particular, no porous fillings are provided in it.

Third solid electrolyte film 23 is equipped on its large surface facing inward from the viewpoint of sensor element 20 (downward in FIG. 1), oppositely to reference gas conduit 35, with a cermet electrode 312 as functional element 31 for measuring an oxygen concentration. A conductor path 328 is attached as a continuation of cermet electrode 312 at its end, the transition from the cermet electrode to conductor path 328 being characterized by a decrease in structure width.

Conductor path 328 has on the exhaust-gas side a portion, referred to as supply lead 327, that in the present case has a constant width. Conductor path 328 furthermore has, facing away from the exhaust gas, a portion referred to as collar 329, which in the present case is embodied annularly (see also FIG. 5). A film binder layer 333 is provided on this side of third solid electrolyte layer 23, at least where otherwise unimprinted.

Figure 2:
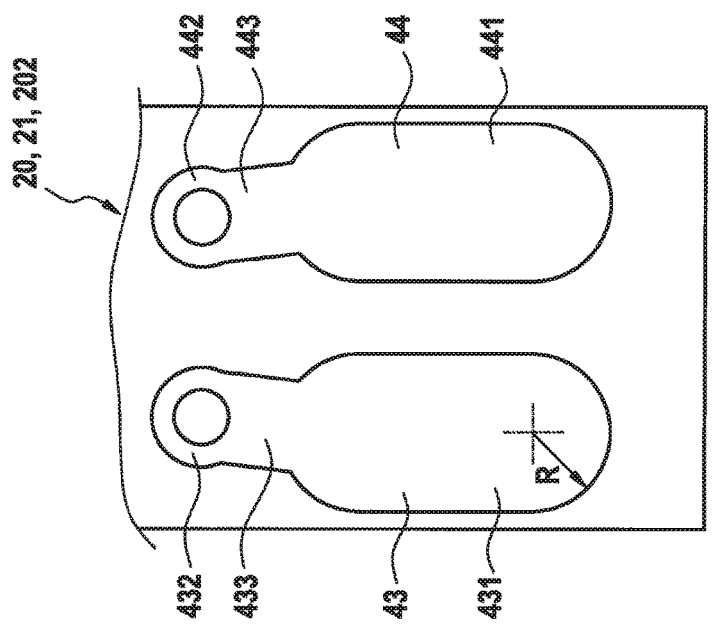
FIGS. 2, 3, 4, 4a, 5, 5a, 6 and 7 are enlarged detail views.

Third solid electrolyte film 23 is equipped, here imprinted, on its large surface facing outward from the viewpoint of sensor element 20 (upward in FIG. 1), in second end region 202 of sensor element 20, with a contact surface 45 and a further contact surface 46 (see also FIG. 2).

Adjoining further contact surface 46 is a conductor path 320 having, for example, a constant width, which extends as far as a further cermet electrode 313 disposed in first end region 201 of sensor element 20. Conductor path 320 is covered with a, for example, sealed cover layer 361; further cermet electrode 313 is equipped with porous layers 362 in order to ensure communication between an external space and further cermet electrode 313.

Third solid electrolyte film 23 has in the second end region a passthrough 503 that proceeds in a vertical direction through third solid electrolyte film 23 and electrically conductively connects contact surface 45 to collar 329 (see FIG. 6).

FIG. 2 is a plan view of third solid electrolyte film 23 showing second end region 202, facing away from the exhaust gas, of sensor element 20. Contact surface 45 is disposed on the left when looking toward first end region 201, facing toward the exhaust gas, of sensor element 20.

Contact surface 45 is made up of three sub-regions, namely a body region 451, a head region 452, and a neck region 453. Body region 451 is disposed on that side of contact surface 45 which faces away from the exhaust gas. It has an elongated basic shape that derives from a rectangle of equal length and width by maximum rounding of the corners, i.e. by rounding with a radius of curvature R that corresponds to half the width of body region 451 or of contact surface 45. Semicircular end regions of body region 451 or of contact surface 45 are thus produced on that side of contact surface 45 which faces away from the exhaust gas.

Based on an unsintered sensor element 20 (sintered: −20%), the length of body region 451 in this example is 2.5 mm or more and the width of body region 451 is 1.5 mm or more. Body region 451 is spaced 0.4 mm or less away from the left outer edge of sensor element 20, and spaced 1.3 mm or less away from the front outer edge of sensor element 20.

Head region 452 is disposed on that side of contact surface 45 which faces toward the exhaust gas. Head region 452 is embodied, for example, annularly, having an inside diameter of 0.5 mm or less and an outside diameter of 1 mm or more, based on an unsintered sensor element 20 (sintered: −20%).

Neck region 453 is embodied between body region 451 and head region 452. It forms, with respect to body region 451 and head region 452, a constriction of contact surface 45 having a minimum width of, in the example, 0.3 mm and a length of 0.3 mm, based on an unsintered sensor element 20 (sintered: −20%).

In the example, body region 451 exhibits a mirror symmetry with reference to an axis that points in the longitudinal direction of sensor element 20. Head region 452 and neck region 453 also exhibit a mirror symmetry, but with reference to an axis that is rotated 9°, in a mathematically negative rotation direction in a plan view of sensor element 20, with respect to the longitudinal axis of sensor element 20, so that head region 452 and neck region 453 as a whole are slightly inclined toward the center of the sensor.

Head region 452 of contact surface 45 interacts electrically conductively with a passthrough 503 through third solid electrolyte layer 23.

In FIG. 2, further contact surface 46 is furthermore disposed on the right next to contact surface 45 when looking toward first end region 201, facing toward the exhaust gas, of sensor element 20. The disposition and size of further contact surface 46 correspond in this regard, i.e. transposing left and right, to the disposition and size of body region 451 of contact surface 45, with the provision that a spacing of at least 0.6 mm exists between contact surface 45 and further contact surface 46, based on an unsintered sensor element 20 (sintered: −20%).

Further contact surface 46 is made up only of a part corresponding to body region 451 of contact surface 45, i.e. has neither a head region nor a neck region. It also does not interact with a passthrough; it is instead contacted directly to conductor path 328 that leads to further cermet electrode 313. A center axis of conductor path 328 in a longitudinal direction is shifted 0.1 to 0.4 mm, in the example 0.2 mm, transversely inward, based on a center axis of further contact surface 46 and based on an unsintered sensor element 20 (sintered: −20%).

Contact surfaces 45, 46 have a noble-metal proportional content of 83% to 87% and a proportional content of ZrO2 and Y2O3 together of 12% to 16 wt %.

In FIG. 3, second end region 202, facing away from the exhaust gas, of sensor element 20 is shown in a bottom view below first solid electrolyte film 21 that faces downward in FIG. 1.

Contact surface 43 is disposed here on the left when looking toward first end region 201, facing toward the exhaust gas, of sensor element 20.

Contact surface 43 is made up of three sub-regions, namely a body region 431, a head region 432, and a neck region 433. Body region 431 is disposed on that side of contact surface 43 which faces away from the exhaust gas. It has an elongated basic shape that derives from a rectangle of equal length and width by maximum rounding of the corners, i.e. by rounding with a radius of curvature R that corresponds to half the width of body region 431 or of contact surface 43. Semicircular end regions of body region 431 or of contact surface 43 are thus produced on that side of contact surface 43 which faces away from the exhaust gas.

Based on an unsintered sensor element 20 (sintered: −20%), the length of body region 431 in this example is 2.5 mm or more, and the width of body region 431 is 1.5 mm or more. Body region 431 is spaced 0.4 mm or less away from the left outer edge of sensor element 20, and spaced 1.3 mm or less away from the front outer edge of sensor element 20.

Head region 432 is disposed on that side of contact surface 43 which faces toward the exhaust gas. Head region 432 is embodied, for example, annularly, having an inside diameter of 0.5 mm or less and an outside diameter of 1 mm or more, based on an unsintered sensor element 20 (sintered: −20%).

Neck region 433 is embodied between body region 431 and head region 432. It forms, with respect to body region 431 and head region 432, a constriction of contact surface 43 having a minimum width of, in the example, 0.9 mm and a length of 0.3 mm, based on an unsintered sensor element 20 (sintered: −20%).

Neck region 433 of contact surface 43 is substantially wider, here by a factor of more than 2, than neck region 451 of contact surface 45 in FIG. 2. The background is that large currents are delivered via contact surface 43 to heating apparatus 311, whereas only comparatively small currents are delivered via contact surface 45 to cermet electrode 312. Contact surface 43 is consequently configured with a decreased ohmic resistance or a widened neck region 433.

In the example, body region 431 exhibits a mirror symmetry with reference to an axis that points in the longitudinal direction of sensor element 20. Head region 432 and neck region 433 also exhibit a mirror symmetry, but with reference to an axis that is rotated 9°, in a mathematically negative rotation direction in a plan view of sensor element 20, with respect to the longitudinal axis of sensor element 20, so that head region 432 and neck region 433 as a whole are slightly inclined toward the center of the sensor.

Head region 432 of contact surface 43 interacts electrically conductively with a passthrough 501 through first solid electrolyte layer 21.

In FIG. 3, further contact surface 44 is furthermore disposed on the right next to contact surface 43 when looking toward first end region 201, facing toward the exhaust gas, of sensor element 20. The disposition and size of further contact surface 44 correspond in this regard, i.e. transposing left and right and transposing the positive and negative rotation direction, to the disposition and size of contact surface 43, with the provision that a spacing of at least 0.6 mm exists between contact surface 43 and further contact surface 44, based on an unsintered sensor element 20 (sintered: −20%).

Contact surfaces 43, 44 have a noble-metal proportional content of 83% to 87% and a proportional content of ZrO2 and Y2O3 together of 12% to 16 wt %.

Figure 4:
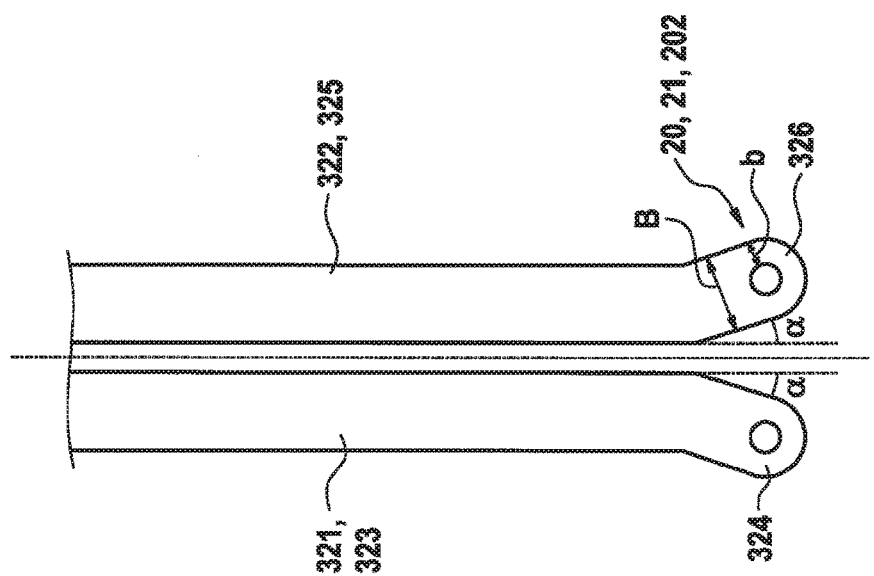

FIG. 4 shows second end region 202, facing away from the exhaust gas, of sensor element 20 in a plan view of first solid electrolyte film 21 (from above in FIG. 1). Conductor path 322 is disposed here on the right when looking toward first end region 201, facing toward the exhaust gas, of sensor element 20. Conductor path 322 is made up of two sub-regions, namely a supply lead 325 and a collar 326.

Supply lead 325 constitutes the exhaust-gas-side part of conductor path 322 and extends from heating apparatus 311 on the exhaust gas side to collar 326 disposed at the end of supply lead 325 facing away from the exhaust gas. In the present case supply lead 325 has a width B of 1.2 mm and extends on the exhaust-gas side with a spacing in a transverse direction of 0.25 mm from the longitudinal center axis of sensor element 20, based in each case on an unsintered sensor element 20 (sintered: −20%). In an end region facing away from the exhaust gas, supply lead 325 is angled to the right (i.e. outward) at an angle of 18°.

Collar 326 is embodied annularly and in the present case describes an arc of 180° whose outside diameter is identical to the width B of supply lead 325 and whose inside diameter is equal to 0.4 mm. A width of the collar is thus 0.3 mm, based in each case on an unsintered sensor element 20 (sintered: −20%). A width ratio of collar width b to supply lead width B is 0.33.

The electrical resistance of passthrough 501 is equal or approximately equal to the electrical resistance of conductor path 322, based on a temperature distribution that can occur or can typically occur during operation of the sensor. In addition to a homogeneous temperature distribution, for example 20° C., it is alternatively also possible to assume in this context temperature distributions that are inhomogeneous. For example, uniform temperature rises in a longitudinal direction of 1100° C. in the region of heating apparatus 311, and 200° C., 300° C., or even 400° C. in the region of passthrough 501, can be taken as a basis.

The electrical resistance of the electrical connection of the functional element, in particular of heating apparatus 311, to contact surface 43 is, for example, in the range of 2.5 ohm at 20° C.

In FIG. 4, conductor path 321 is furthermore disposed symmetrically with reference to the longitudinal center axis with respect to conductor path 322 when looking toward first end region 201, facing toward the exhaust gas, of sensor element 20. The disposition and size of conductor path 31 correspond in this regard, i.e. transposing left and right, to the disposition and size of conductor path 322.

Supply leads 325, 323 have a noble-metal proportional content of more than 95 wt %, for example 98 wt %, and at least 1 wt % Al2O3.

The electrical resistance of passthrough 502 is equal or approximately equal to the electrical resistance of conductor path 321, based on a temperature distribution that can occur or can typically occur during operation of the sensor. In addition to a homogeneous temperature distribution, for example 20° C., it is alternatively also possible to assume in this context temperature distributions that are inhomogeneous. For example, uniform temperature rises in a longitudinal direction of 1100° C. in the region of heating apparatus 311, and 200° C., 300° C., or even 400° C. in the region of passthrough 501, can be taken as a basis.

Figure 4A:
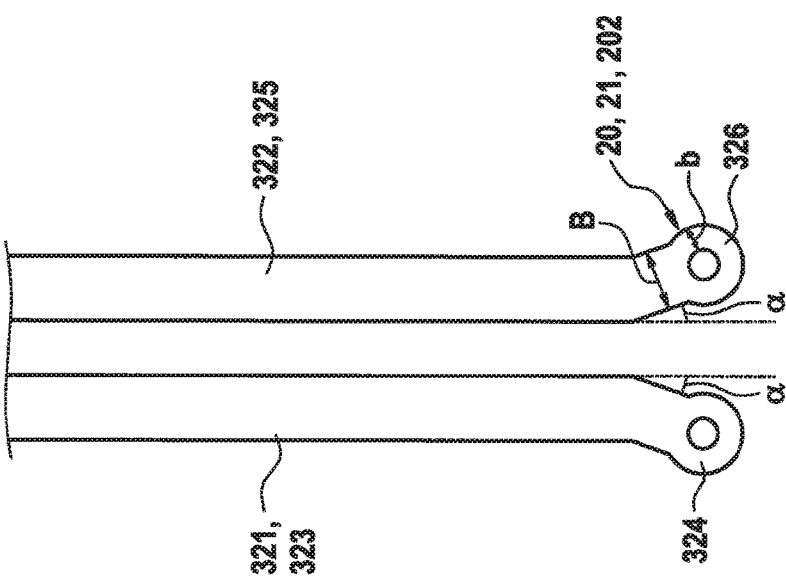

FIG. 4a shows, as a variant, a sensor element 20 having slightly modified supply leads 323, 325, the modification consisting merely in the fact that the width B of supply leads 323, 325 is equal to only 1.08 mm rather than 1.2 mm, i.e. is reduced slightly (10%) as compared with collar 324, 326. The metric dimensions are based on an unsintered sensor element 20 (sintered: −20%).

Figure 5:
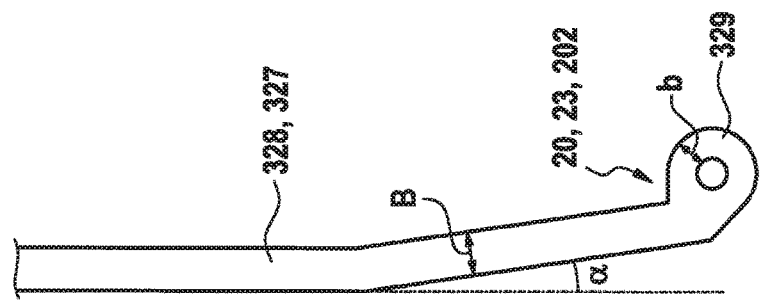

FIG. 5 shows second end region 202, facing away from the exhaust gas, of sensor element 20 in a bottom view below third solid electrolyte film 23 (from below in FIG. 3). Here conductor path 322 is disposed on the right when looking toward first end region 201, facing toward the exhaust gas, of sensor element 20. Conductor path 322 is made up of two sub-regions, namely a supply lead 327 and a collar 329.

Supply lead 327 constitutes the exhaust-gas-side part of the conductor path and extends from cermet electrode 312 on the exhaust-gas side to collar 329, disposed on the side of supply lead 327 facing away from the exhaust gas. In the present case the supply lead has a width B of 0.4 mm (unsintered; sintered: −20%), and extends on the exhaust-gas side in such a way that in a vertical projection looking onto sensor element 20, it is disposed inside reference gas conduit 35. This part of supply lead 327 is thus largely protected from crushing during the production process.

In an end region facing away from the exhaust gas, supply lead 327 is angled to the right, i.e. outward, at an angle of no more than 25°, here of 8°. In this end region facing away from the exhaust gas, the supply lead intersects with the edge of reference gas conduit 35 in a vertical projection looking onto sensor element 20. The comparatively small intersection angle results in a long overlap zone between conductor path 328 and the edge of reference gas conduit 35, and thus once again in good protection of supply lead 327 from crushing during the production process.

Collar 329 is embodied annularly. A width of collar b is 0.3 mm, based on an unsintered sensor element 20 (sintered: −20%). A width ratio of collar width b to supply lead width B is 0.75.

Supply lead 327 has a noble-metal proportional content of 83 wt % to 87 wt %, and a proportional content of ZrO2 and Y2O3 together of 12 wt % to 16 wt %.

The electrical resistance of passthrough 503 is equal or approximately equal to the electrical resistance of conductor path 328, based on a temperature distribution that can occur or can typically occur during operation of the sensor. In addition to a homogeneous temperature distribution, for example 20° C., it is alternatively also possible to assume in this context temperature distributions that are inhomogeneous. For example, uniform temperature rises in a longitudinal direction of 750° C. in the region of cermet electrode 312, and 200° C., 300° C., or even 400° C. in the region of passthrough 503, can be taken as a basis.

Figure 5A:
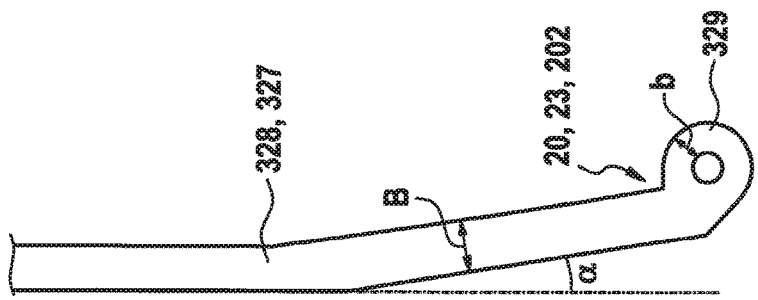

FIG. 5a shows, as a variant, a sensor element 20 having a slightly modified supply lead 328, the modification consisting merely in the fact that the width B of supply lead 328 in the end region facing away from the exhaust gas is increased by 50%, from 0.4 mm to 0.6 mm, as compared with the region of supply lead 328 facing toward the exhaust gas. The metric dimensions are based on an unsintered sensor element 20 (sintered: −20%).

A section through sensor element 20 shown in the preceding FIGS. 1 to 5, in a plane perpendicular to the longitudinal direction of sensor element 20 and through passthroughs 501, 502, 503, is shown purely schematically in FIG. 6.

Passthroughs 501, 502, 503 are embodied as a conductive coating of the radial wall of a through-plated hole 601, 602, 603 of sensor element 20. In the example, the diameter of through-plated holes 601, 602, 603 is 0.6 mm, based on an unsintered sensor element 20 (sintered: −20%, i.e. 0.48 mm).

It is evident that passthroughs 501, 502, 503 are each embodied non-overlappingly with reference to gas conduit 35 in a plan view onto sensor element 20.

Passthroughs 501, 502, 503 have a noble-metal proportional content of 83 wt % to 87 wt % and a proportional content of ZrO2 and Y2O3 together of 3 wt % to 8 wt %, and additionally a proportional content of Nb2O5 of 6 wt % to 12 wt %.

Figure 7:
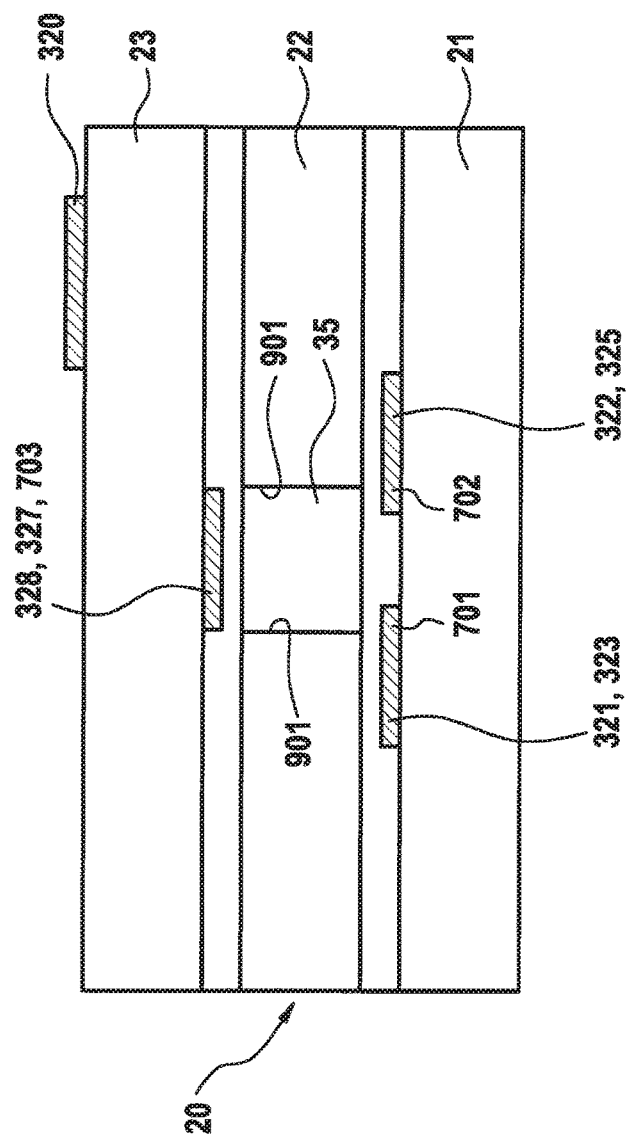

A section through sensor element 20 shown in the preceding FIGS. 1 to 5, in a plane perpendicular to the longitudinal direction of sensor element 20 approximately in the region of half the longitudinal extent of sensor element 20, is shown purely schematically in FIG. 7.

As is evident, conductor path 328 and supply lead 327 that lead to cermet electrode 312 have, in a plan view onto sensor element 20, an overlap 703 over their entire width with reference conduit 35. In addition, conductor paths 321, 322, and supply leads 323, 325 that lead to the resistance heater, have a respective overlap 701, 702 with reference conduit 35 over approximately 10% of their width.

What is claimed is:

1. A sensor element, comprising:
a first end region;
a second end region, wherein the end regions are located oppositely from one another in a longitudinal direction;
a functional element, in the first end region, that is electrically conductively connected to a contact surface disposed in the second end region on the outer surface of the sensor element;
wherein the contact surface has a rounding on its side facing away from the first end region,
wherein the contact surface has a body region, a head region, and a neck region, the body region being disposed on the side of the contact surface which faces away from the first end region and is at least substantially oval; the head region being disposed on the side of the contact surface which faces toward the first end region and is at least substantially circular or annular; the neck region, in which the width of the contact surface is less than in the body region and in the head region, being disposed between the body region and the head region,
wherein a radius of curvature of the rounding is not less than 6% of the width of the sensor element.

2. The sensor element of claim 1, wherein a radius of curvature of the rounding is equal to not less than 0.3 mm.

3. The sensor element of claim 1, wherein a radius of curvature of the rounding is not less than 15% of the width of the contact surface.

4. The sensor element of claim 1, wherein the body region of the contact surface has a first axis of symmetry that extends in a longitudinal direction of the sensor element; and the head region and the neck region of the contact surface have a common second axis of symmetry; and the first axis of symmetry and second axis of symmetry enclose an angle of 5° to 25°.

5. The sensor element of claim 4, wherein the contact surface is disposed off-center in a transverse direction of the sensor element; and the head region and neck region are disposed, when viewed from the body region, with an inclination toward the center in the transverse direction of the sensor element.

6. The sensor element of claim 1, wherein a further contact surface is disposed in the second end region of the sensor element alongside the contact surface; the further contact surface being electrically conductively connected to the functional element and/or to a further functional element; a radius of curvature of the rounding being not less than 10% of the spacing between the contact surface and the further contact surface.

7. The sensor element of claim 6, wherein a radius of curvature of the rounding is not less than the spacing between the contact surface and the further contact surface.

8. The sensor element of claim 6, wherein the contact surface and the further contact surface are mirror-symmetrical with respect to an axis that extends in a longitudinal direction of the sensor element.

9. The sensor element of claim 1, wherein the functional element is disposed in the interior of the sensor element; the electrically conductive connection between the functional element and the contact surface having a conductor path extending in the interior of the sensor element substantially in a longitudinal direction, and having a passthrough that extends substantially perpendicularly to the longitudinal direction and to the transverse direction of the sensor element.

10. The sensor element of claim 1, wherein the sensor element is for detection of a physical property of a gas.

11. The sensor element of claim 1, wherein the sensor element is for detection of the concentration of a gas component or of the temperature or of a solid constituent or of a liquid constituent of an exhaust gas of an internal combustion engine.

12. The sensor element of claim 1, wherein a radius of curvature of the rounding is equal to not less than 0.6 mm.

13. The sensor element of claim 1, wherein a radius of curvature of the rounding is not less than 30% of the width of the contact surface.

14. The sensor element of claim 1, wherein the body region of the contact surface has a first axis of symmetry that extends at least substantially in a longitudinal direction of the sensor element; and the head region and the neck region of the contact surface have a common second axis of symmetry; and the first axis of symmetry and second axis of symmetry enclose an angle of 5° to 25°.

15. The sensor element of claim 1, wherein a further contact surface is disposed in the second end region of the sensor element alongside the contact surface; the further contact surface being electrically conductively connected to the functional element and/or to a further functional element; a radius of curvature of the rounding being not less than 30% of the spacing between the contact surface and the further contact surface.

16. The sensor element of claim 1, wherein a planar area of the contact surface is 2% or less of a planar area of a largest surface of the sensor element.

17. A sensor, comprising:
a sensor element, including:
  a first end region and a second end region, wherein the end regions are located oppositely from one another in a longitudinal direction;
  a functional element, in the first end region, that is electrically conductively connected to a contact surface disposed in the second end region on the outer surface of the sensor element;
  wherein the contact surface has a rounding on its side facing away from the first end region; and
a metallic contact element that electrically contacts the sensor element at the contact surface, nonpositively and/or positively, from outside the sensor element,
wherein the contact surface has a body region, a head region, and a neck region, the body region being disposed on the side of the contact surface which faces away from the first end region and is at least substantially oval; the head region being disposed on the side of the contact surface which faces toward the first end region and is at least substantially circular or annular; the neck region, in which the width of the contact surface is less than in the body region and in the head region, being disposed between the body region and the head region,
wherein a radius of curvature of the rounding is not less than 12% of the width of the sensor element.

* * * * *